United States Patent
Sahouani et al.

(10) Patent No.: US 8,767,133 B2
(45) Date of Patent: Jul. 1, 2014

(54) OPTICAL CONTROL DEVICES AND METHODS OF MAKING

(75) Inventors: Hassan Sahouani, Hastings, MN (US); Feng Bai, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 428 days.

(21) Appl. No.: 13/202,024

(22) PCT Filed: Feb. 10, 2010

(86) PCT No.: PCT/US2010/023732
§ 371 (c)(1),
(2), (4) Date: Aug. 17, 2011

(87) PCT Pub. No.: WO2010/096310
PCT Pub. Date: Aug. 26, 2010

(65) Prior Publication Data
US 2011/0299025 A1    Dec. 8, 2011

Related U.S. Application Data

(60) Provisional application No. 61/152,999, filed on Feb. 17, 2009.

(51) Int. Cl.
G02F 1/1335 (2006.01)
G02F 1/1333 (2006.01)
G02F 1/1337 (2006.01)
C09K 19/60 (2006.01)
G02F 1/13 (2006.01)

(52) U.S. Cl.
USPC .............. 349/14; 349/96; 349/122; 349/123; 349/162; 349/165; 349/194

(58) Field of Classification Search
USPC .............. 349/13, 14, 96, 122, 123, 139, 158, 349/162, 165, 194
See application file for complete search history.

(56) References Cited

U.S. PATENT DOCUMENTS

| | | | |
|---|---|---|---|
| 4,071,912 | A | 2/1978 | Budmiger |
| 5,074,647 | A | 12/1991 | Fergason |
| 5,085,498 | A | 2/1992 | Yamamoto |
| 5,693,446 | A | 12/1997 | Staral |
| 5,793,449 | A | 8/1998 | Lagerwall |
| 6,245,399 | B1 | 6/2001 | Sahouani |

(Continued)

FOREIGN PATENT DOCUMENTS

| | | |
|---|---|---|
| CN | 10-113-7932 | 3/2008 |
| JP | 9288264 | 11/1997 |

(Continued)

*Primary Examiner* — Lucy Chien
*Assistant Examiner* — Paisley L Arendt
(74) *Attorney, Agent, or Firm* — Kenneth B. Wood

(57) ABSTRACT

Herein are disclosed methods by which a layer of oriented chromonic material may be transferred from a flexible substrate to a receiving substrate, so as to form a subassembly for use in the assembly of liquid crystal cells. The oriented chromonic material layer may function as an alignment layer for aligning liquid crystal material, and may also incorporate a pleochroic dye so to function as a polarizing layer. An oriented chromonic material layer of relatively large area can be transferred, which enables the production of relatively large liquid crystal cells for use in, e.g., autodarkening filters such as used for eye protection in welding operations. Curved liquid crystal cells are also disclosed.

15 Claims, 8 Drawing Sheets

(56) References Cited

U.S. PATENT DOCUMENTS

| | | |
|---|---|---|
| 6,395,354 B1 | 5/2002 | Sahouani |
| 6,399,166 B1 * | 6/2002 | Khan et al. ............... 428/1.31 |
| 6,488,866 B1 | 12/2002 | Sahouani |
| 6,538,714 B1 | 3/2003 | Sahouani |
| 6,673,398 B2 * | 1/2004 | Schneider et al. ............ 428/1.2 |
| 6,699,533 B2 | 3/2004 | Sahouani |
| 6,841,320 B2 | 1/2005 | Lazarev |
| 6,848,897 B2 | 2/2005 | Lazarev |
| 7,755,737 B2 | 7/2010 | Taniguchi |
| 2003/0052838 A1 | 3/2003 | Kim |
| 2004/0191428 A1 | 9/2004 | Tsuda |
| 2004/0201795 A1 | 10/2004 | Paukshto |
| 2005/0140837 A1 | 6/2005 | Crawford |
| 2005/0164470 A1 | 7/2005 | Yamazaki |

FOREIGN PATENT DOCUMENTS

| | | |
|---|---|---|
| JP | 2001-356342 | 12/2001 |
| WO | 01/35161 | 5/2001 |
| WO | 02/44802 | 6/2002 |
| WO | 03/065107 | 8/2003 |
| WO | WO 2004/053586 A1 | 6/2004 |
| WO | WO 2004/097505 A2 | 11/2004 |
| WO | WO 2005/061239 A2 | 7/2005 |
| WO | WO 2008/033291 A2 | 3/2008 |
| WO | WO 2008/130480 A1 | 10/2008 |

* cited by examiner

1

OPTICAL CONTROL DEVICES AND METHODS OF MAKING

CROSS REFERENCE TO RELATED APPLICATIONS

This application is a national stage filing under 35 U.S.C. 371 of PCT/US2010/023732, filed Feb. 10, 2010, which claims priority to U.S. Provisional Application No. 61/152,999, filed Feb. 17, 2009, the disclosures of which are incorporated by reference in their entirety herein.

BACKGROUND

So-called automatic darkening filters are often used for applications such as welding, where protection from intense levels of incident light is desired. A typical automatic darkening filter can be controllably changed from a light (relatively transparent) state when not subjected to high intensity light, to a dark (relatively opaque) state upon exposure to such light. Such automatic darkening filters are often constructed from a combination of one or more polarizing layers and one or more liquid crystal cells, aligned in the same optical path.

In a liquid crystal cell, the molecules of liquid crystal material are typically aligned in a preferred direction. This alignment is often accomplished through the use of an alignment layer on each side of the liquid crystal material. Alignment layers are often polymeric films, (e.g. polyimides), that are mechanically rubbed in a single direction to provide an oriented structure that imparts an aligning effect on the liquid crystal material. The alignment of the liquid crystal material can then be altered by the imposition of an electric field, in order to manipulate the optical transmissivity of the cell.

Chromonic materials, when deposited and dried so as to form a highly oriented structure, have found use as alignment layers in liquid crystal cells. Also, pleochroic dyes have been incorporated into chromonic materials, such that the dried and oriented chromonic material may function as a polarizing layer. Thus, chromonic materials with pleochroic dyes therein may provide a single layer that can serve as a combined alignment/polarizer layer.

SUMMARY

Herein are disclosed methods by which a layer of oriented chromonic material may be formed (e.g., coated and dried) on a flexible substrate and then physically transferred therefrom to a receiving substrate, so as to form an alignment layer for use in a liquid crystal cell. If a pleochroic dye is present in the chromonic material, the oriented chromonic material can serve as a polarizing layer for use in a liquid crystal cell. Also disclosed herein are curved liquid crystal cells.

Thus in one aspect, herein is disclosed an optical control device comprising an optically clear first substrate comprising at least a curved first major surface; a conductive layer adjacent the curved first major surface of the first substrate; an alignment-polarizer layer adjacent the conductive layer, wherein the alignment-polarizer layer comprises an oriented chromonic material that further comprises at least one pleochroic dye; an optically clear second substrate comprising at least a curved first major surface, wherein the curved first major surface of the first substrate, and the curved first major surface of the second substrate, are mated so as to define a cavity therebetween; and, a liquid crystal material layer between the alignment-polarizer layer and the curved first major surface of the second substrate and the liquid crystal material layer being in contact with the alignment-polarizer layer.

Thus in another aspect, herein is disclosed a method of manufacturing an optical control device, the method comprising: providing a flexible substrate; depositing a chromonic material on the flexible substrate and drying the chromonic material so as to form an oriented chromonic material layer; providing a first substrate with at least a first major surface; providing a curable adhesive layer and a conductive layer, between the oriented chromonic material layer and the first major surface of the first substrate; bringing the flexible substrate with the oriented chromonic material layer thereupon together with the first major surface of the first substrate, the curable adhesive layer, and the conductive layer, so as to form a laminate structure; curing the adhesive; and, separating the flexible substrate from the oriented chromonic material layer These and other features and aspects of the present description will be more fully understood from the following detailed description of exemplary embodiments. It should be understood that the foregoing descriptions and the following detailed descriptions are exemplary and are not restrictive of the present description.

Figure 1:
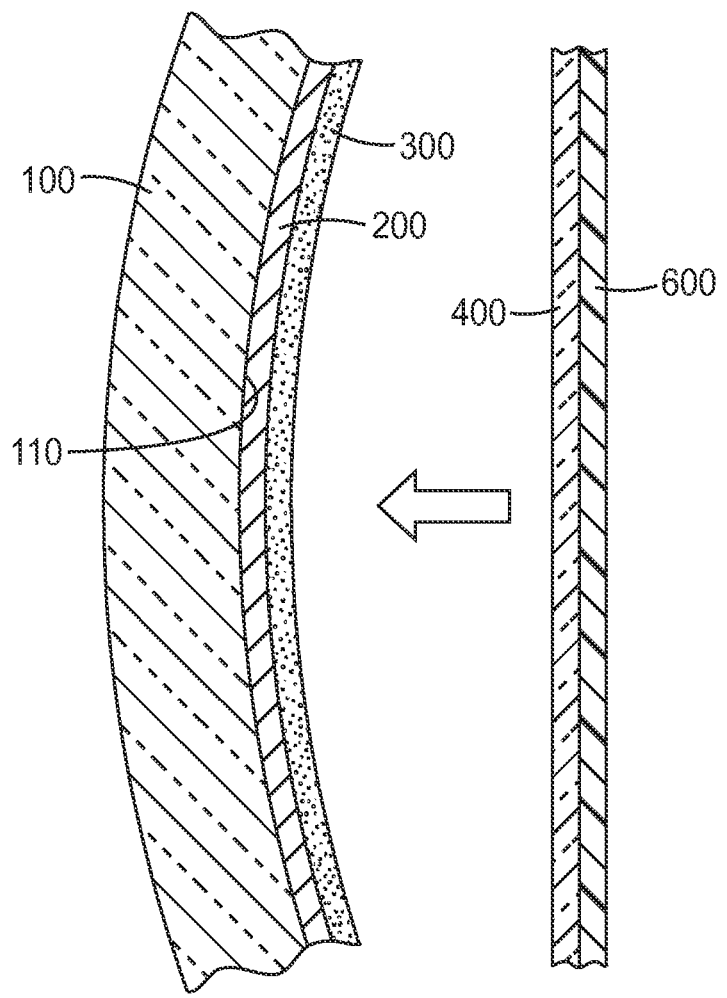
FIG. 1 is a side schematic cross sectional view illustrating an exemplary method disclosed herein.

Drawings and elements therein are not to scale unless noted. In the Figures, like reference numerals are used to designate like features throughout. Although terms such as "top", bottom", "upper", lower", "over", "under", "front", "back", and "first" and "second" may be used in this disclosure, it should be understood that those terms are used in their relative sense only, unless noted herein. In particular, it is noted that the term "adjacent", as used herein with respect to layers, signifies layers that are located physically near each other but does not exclude the presence of one or more additional layers in between the layers described as adjacent. The term "disposed" as used herein with respect to layers, signifies layers that are located physically near each other and in contact with each other.

DETAILED DESCRIPTION

Herein are disclosed methods by which a layer of oriented chromonic material can be formed on a flexible substrate and then transferred therefrom to a receiving substrate, and the flexible substrate then removed, so as to form a subassembly that may find use in the assembly of e.g. liquid crystal cells.

The term "chromonic" is defined herein as a non-polymeric molecule that comprises a hydrophobic core portion comprising multiple aromatic and/or heteroaromatic rings, with multiple hydrophilic substituents arranged around the periphery of the hydrophobic core portion and connected thereto by covalent bonds, wherein when in aqueous solution the molecules aggregate into columns rather than into micelles and do not exhibit a critical micelle concentration or a Krafft temperature.

Chromonic materials have been described, for example, in Attwood, T. K., and Lydon, T. E.; *Molec. Crystals. Liq. Crystals,* 108, 349 (1984). When in aqueous solution, the chromonic materials tend to aggregate into a nematic ordering characterized by a long-range order. Such molecular stacking can take on a number of morphologies, but is typically characterized by a tendency to form columns created by a stack of molecular layers (owing to the above-described structure of chromonic molecules). Ordered stacks of molecules are formed that grow with increasing concentration in solution, but they are distinct from micellar phases, in that they generally do not have surfactant-like properties and do not exhibit a critical micellar concentration. This results from the fact that (unlike conventional amphiphilic molecules that typically comprise one or more hydrophilic "head" portions and one or more hydrophobic "tail" portions such that in solution the hydrophobic portions of multiple molecules can cluster so as to promote the formation of micelles), chromonic molecules comprise hydrophilic moities that are arranged (e.g., spaced) around the periphery of a hydrophobic core. Such a structure promotes the formation of columns rather than of micelles.

In certain embodiments, the chromonic molecules comprise a hydrophobic core portion comprising 3, 4, or 5 aromatic rings and/or nitrogen-substituted aromatic rings, with at least two (hydrophilic) carboxyl groups being covalently bonded to separate rings of the core portion.

In some embodiments, the chromonic molecule may contain at least one formal positive charge. For example, the chromonic molecule may be zwitterionic, with at least one formal positive, and at least one formal negative charge. In some chromonic molecules, the negative charge can be carried by an acidic group having a dissociated hydrogen atom such as a carboxyl group in its basic form, (i.e., —COO$^-$). The negative charge can be carried by multiple carboxyl functional groups present, such that a proper representation of the chromonic molecule has two or more resonance structures, or structural isomers.

In further embodiments, chromonic molecules may include triazine derivatives with the structure shown in Formula I.

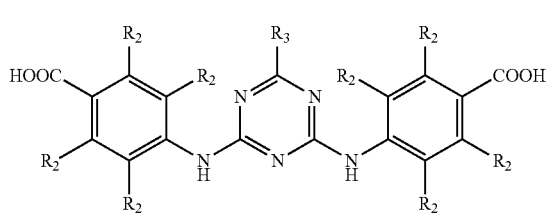

I

The compounds of Formula I have an orientation such that the carboxyl (—COOH) group may be para with respect to the amino linkage to the triazine center of the compound. Although the chromonic molecule is neutral as depicted in Formula I, it may exist in alternative forms, such as a zwitterion or as a proton tautomer. For example, a hydrogen atom can be dissociated from one of the carboxyl groups, and can be associated with one of the nitrogen atoms in the triazine ring or with one of the amino linkages. Further, the chromonic molecule may also be a salt. The carboxyl group may also be meta with respect to the amino linkage, as shown in Formula II, or it may be a combination of para and meta orientations.

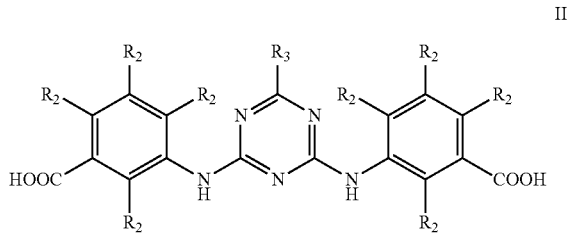

II

Each $R_2$ of Formulas I and II may be independently selected from any electron donating group, electron withdrawing group, electron neutral group, or combinations thereof. In some embodiments, $R_2$ may be hydrogen, a substituted or unsubstituted alkyl group, a substituted or unsubstituted alkoxy group (i.e., an alkoxy group having a formula —OR where R is an alkyl), a substituted or unsubstituted carboxyalkyl group (i.e., a carboxyalkyl group having a formula —(CO)OR where (CO) denotes a carbonyl and R is an alkyl), or combinations thereof. Suitable substituents include hydroxyl, alkoxy, carboxyalkyl, sulfonate, halide functional groups, or combinations thereof. In one embodiment, $R_2$ may be hydrogen.

Group $R_3$ of Formulas I and II may be selected from a substituted heteroaromatic ring, unsubstituted heteroaromatic ring, a substituted heterocyclic ring, or an unsubstituted heterocyclic ring that is linked to the triazine group through a nitrogen atom within the ring of $R_3$. As used herein, the term heterocyclic refers to as an hydrophilic organic compound having a ring structure that includes a heteroatom such as oxygen, nitrogen, sulfur, wherein the ring structure can be saturated or partially saturated. As used herein, the term "heteroaromatic refers to an organic compound having a ring structure that includes a heteroatom such as oxygen, nitrogen, or sulfur, wherein the ring structure is unsaturated.

$R_3$ can be, but is not limited to, a heteroaromatic ring derived from pyridine, pyridazine, pyrimidine, pyrazine, imidazole, oxazole, isoxazole, thiazole, oxadiazole, thiadiazole, pyrazole, triazole, triazine, quinoline, or isoquinoline. In many embodiments, $R_3$ includes a heteroaromatic ring derived from pyridine or imidazole. A substituent for the heteroaromatic ring $R_3$ may be selected from, but is not limited to, any of the following substituted and unsubstituted groups: alkyl, carboxyl, amino, alkoxy, thio, cyano, carbonylaminoalkyl (i.e., a group having a formula —(CO)NHR where (CO) denotes a carbonyl and R is an alkyl), sulfonate, hydroxy, halide, perfluoroalkyl, aryl, alkoxy, or carboxyalkyl. In some embodiments, a substituent for $R_3$ may be selected from alkyl, sulfonate, carboxyl, halide, perfluoroalkyl, aryl, alkoxy, or alkyl substituted with hydroxyl, sulfonate, carboxyl, halide, perfluoroalkyl, aryl, or alkoxy.

In some embodiments, $R_3$ may be derived from a substituted pyridine with the substituent being preferably located at the 4-position. In other embodiments, $R_3$ may be derived from a substituted imidazole with the substituent being preferably located at the 3-position. Suitable examples of $R_3$ may include, but are not limited to: 4-(dimethylamino)pyridium- 1-yl, 3-methylimidazolium-1-yl, 4-(pyrrolidin-1-yl)pyridium-1-yl, 4-isopropylpyridinium-1-yl, 4-[(2-hydroxyethyl)methylamino]pyridinium-1-yl, 4-(3-hydroxypropyl)pyridinium-1-yl, 4-methylpyridinium-1-yl, quinolinium-1-yl, 4-tert-butylpyridinium-1-yl, and 4-(2-sulfoethyl)pyridinium-1-yl, as illustrated in Formulas IV to XIII below. Examples of heterocyclic rings that $R_3$ may be selected from include, for example, morpholine, pyrrolidine, piperidine, or piperazine.

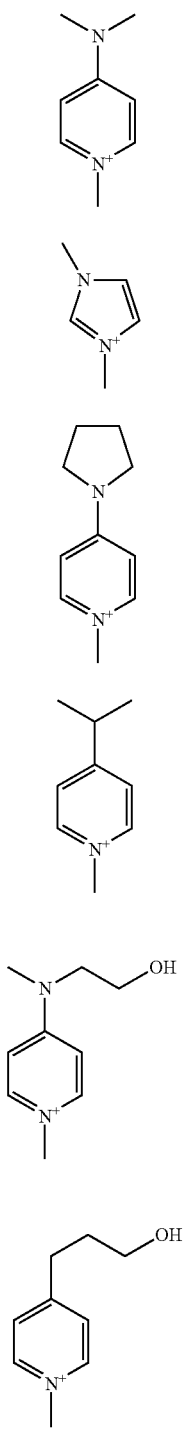

IV

V

VI

VII

VIII

IX

-continued

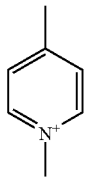

X

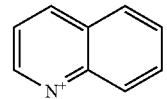

XI

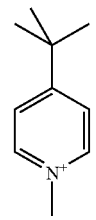

XII

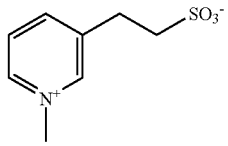

XIII

Some exemplary $R_3$ groups are of Formula XIV,

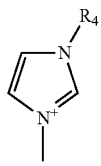

XIV where $R_4$ of Formula XIV may be hydrogen, a substituted alkyl group, or an unsubstituted alkyl group. In some embodiments, $R_4$ may be hydrogen, an unsubstituted alkyl group, or an alkyl group substituted with a hydroxy, an alkoxy, a carboxyalkyl, a sulfonate, or a halide functional group. In other embodiments, $R_4$ may be methyl, propylsulfonic acid, or oleyl (i.e., fatty alcohol). Formula V may be a subset of Formula XIV where $R_4$ is methyl. As depicted above, the chromonic molecules of Formula I or II are neutral; however, chromonic molecules described herein may exist in an ionic form having one formal positive charge. One example of a chromonic molecule is 4-dimethylamino-1-[4,6-di(4-carboxyphenylamino)-1,3,5-triazin-2-yl]pyridium chloride (Formula III) as described in U.S. Pat. No. 6,488,866. In the chromonic compound shown in Formula III, $R_3$ is a dimethylamino substituted pyridine ring linked to the triazine group through the nitrogen atom of the pyridine ring. As shown, the pyridine nitrogen carries a positive charge, and a chloride ion carries a negative charge.

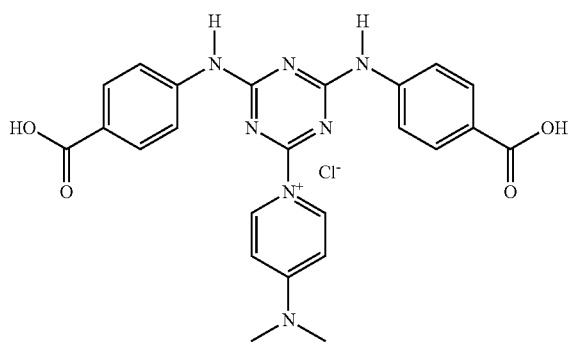

III

The chromonic molecule shown in Formula III may also exist in other tautomeric forms, such as where one or both carboxyl functional groups carry a negative charge and where positive charges are carried by one of the nitrogen atoms in the triazine group and the nitrogen on the pyridine group. In another embodiment, the chromonic molecule may be zwitterionic, such as 4-({4-[(4-carboxylphenyl)amine]-6-[4-(dimethylamino)pyridinium-1-yl]-1,3,5-triazin-2-yl} amino)benzoate as described in U.S. Pat. No. 5,948,487 (Sahouani et al.).

U.S. Pat. No. 5,948,487 (Sahouani et al.) describes triazine derivatives of Formula I prepared as aqueous solutions or as salts, which can later be re-dissolved to form an aqueous solution. A typical synthetic route for the triazine molecules shown in Formula I above involves a two-step process. Cyanuric chloride may be treated with 4-aminobenzoic acid to give 4-{[4-(4-carboxyanilino)-6-chloro-1,3,5-triazin-2-yl]amino}benzoic acid. This intermediate may be treated with a substituted or unsubstituted nitrogen-containing heterocycle. The nitrogen atom of the heterocycle may displace the chlorine atom on the triazine to form a corresponding chloride salt. The zwitterionic derivative of Formula III may be prepared by dissolving the chloride salt in ammonium hydroxide, passing it through an anion exchange column to replace the chloride with hydroxide, and removing the solvent. Alternative structures, as in Formula II, may be obtained by using 3-aminobenzoic acid instead of 4-aminobenzoic acid.

In various embodiments, chromonic materials as disclosed herein, may comprise a molecular weight of at most about 2400, at most about 1600, or at most about 800.

In particular embodiments, chromonic materials as disclosed herein are substantially optically clear; that is, they do not significantly absorb visible light. In such embodiments, chromonic materials are distinguished from materials such as dyes (e.g., compounds that preferentially absorb light of certain wavelengths).

Certain substances may be added to chromonic materials to impart additional functionality to the coated and dried chromonic layer. Thus, in some embodiments, the chromonic material comprises at least one dye. In specific embodiments, the chromonic material comprises at least one pleochroic dye (the term pleochroic meaning that the light absorption of the dye molecule varies as a function of the orientation of the molecule with respect to the polarization of incident light). The use of such a pleochroic dye enables the chromonic material (once oriented/dried as disclosed later herein) to be used (e.g., instead of or in addition to its function as an alignment layer for a liquid crystal material), as a polarizer layer, thus potentially eliminating the need for a separate polarizing layer in a liquid crystal cell. Pleochroic dyes which may be used with the disclosures herein include parallel-colorless dyes and perpendicular-colorless dyes. Suitable dyes may include, for example, the materials available from Sensient Technologies, Milwaukee, Wis., under the trade designations Direct Red 79 and Direct Blue 199.

In some embodiments, the chromonic material comprises at least one non-orienting (e.g., non-pleochroic) dye. Such dyes may be used to provide color filtration capability, infrared filtration capability, etc. In particular, one or more non-orienting dyes may be combined with one or more pleochroic dyes to provide e.g., color polarizers exhibiting a wide range of spectral characteristics. Suitable non-orienting dyes may include for example the materials available from Sensient Technologies under the trade designation Direct Blue 9.

A chromonic composition as described above can be applied, e.g. coated, onto the surface of a substrate. To form a coating composition, a chromonic material may be dissolved into an aqueous solution, optionally in the presence of one or more pH-adjusting compounds (the addition of pH-adjusting compounds may allow the chromonic material to become more soluble in aqueous solution). Suitable pH-adjusting compounds include any known base such as, for example, ammonium hydroxide or various amines. Often, the chromonic materials are dissolved in the aqueous solution at a temperature less than about 40° C. (e.g., at room temperature), and adjusted to a pH of around 7-10 by the addition of base.

One or more optional surfactants may be added to the coating composition to promote wetting of the coating composition onto the surface of a substrate. Suitable surfactants include ionic surfactants, non-ionic surfactants, or combinations thereof. Optional water-soluble polymeric additives useful as viscosity modifiers (e.g., polyethylene glycol) or binders (e.g., low molecular weight hydrolyzed starches) may also be added. In various embodiments, such optional additives or surfactants may be present in the coating composition at an amount corresponding to at least 0.01, at least 0.05, or at least 0.1, weight percent (relative to the dried coating weight of the chromonic material). In further embodiments, the optional additives or surfactants may be present in the coating composition at an amount corresponding to at most 1.0, at most 0.5, or at most 0.3, weight percent (relative to the dried coating weight of the chromonic material). In some embodiments, one or more organic solvents may be added to the coating composition. In various embodiments, the organic solvents may be added to the coating composition to achieve an organic solvent concentration of at least 0.1, at least 0.5, at least 1, at least 3, or at least 5 weight percent of the coating composition. In further embodiments, the organic solvents may be added to the coating composition to achieve an organic solvent concentration up to 10, up to 9, up to 8, or up to 7 weight percent of the coating composition.

The coating composition may also comprise the above-described pleochroic dyes and/or non-orienting dyes so as to provide desired optical functionality to the dried, oriented chromonic material layer.

The coating composition may be applied to a substrate by any suitable method that provides for the ordered arrangement of the chromonic materials; for example, by coating techniques such as wirewound coating rod or extrusion (e.g., using a high precision extrusion die) methods. In some embodiments, orientation (e.g., shear orientation or magnetic orientation) is applied to the coating composition during and/or after application. Such application of shear force can help promote orientation of the molecules of chromonic material such that, upon drying, an oriented structure is obtained.

The coating composition may be applied to a substrate at any useful wet coating thickness. In various embodiments, the coating composition may be applied to the substrate at a uniform wet coating thickness of at least 1, at least 3, at least 5, or at least 10 microns. In further embodiments, the coating composition may be applied to the substrate at a uniform wet coating thickness of up to 25, up to 20, up to 15, or up to 12 microns.

Upon the removal of a substantial amount of water (and any volatile organic solvent, if present) from the coated chromonic material, the molecules of chromonic material may form a highly oriented structure, e.g. that is capable of functioning as an alignment layer for a liquid crystal material that is in contact with the layer of dried chromonic material. Drying of the coated layer may be achieved using any suitable drying method that will allow the chromonic material to form and/or maintain such an oriented structure. Particularly useful drying methods are those that do not damage the coating or significantly disrupt any orientation that is imparted to the oriented chromonic material during coating or deposition. In various specific embodiments, the coated material is dried so as to contain at most 1.0, at most 0.5, or at most 0.1, weight percent water.

In various embodiments, the thickness of the dried, oriented chromonic material layer may be at least 0.5, 1.0, or 2 microns. In further embodiments, the thickness of the dried, oriented chromonic material layer may be at most about 15, 10 or 5.0 microns.

Optionally, the resulting dried oriented chromonic material can be covalently crosslinked, for example by the use of e.g., multifunctional amines that can react with the carboxylic acid moiety of certain chromonic materials thus forming amide linkages. In a specific embodiment, the dried oriented chromonic material is transferred from an initial casting substrate (e.g., the below-described flexible substrate) onto a receiving substrate prior to crosslinking.

Optionally, the resulting oriented chromonic material can be non-covalently crosslinked, for example by exposing the chromonic material to multivalent cations. Again, such process may be carried out after the oriented chromonic material is transferred from an initial casting substrate to a receiving substrate.

The chromonic materials described above, containing one or more dyes as described above, may be deposited onto a flexible substrate and dried to form an oriented chromonic material layer. Suitable flexible substrates include those comprising at least one major surface onto which the chromonic material can be deposited (e.g., by shear coating) and dried so as to form an oriented chromonic material. Particularly suitable flexible substrates comprise at least one major surface that does not unacceptably alter or reduce the tendency of the chromonic material to form an oriented structure when shear coated onto the major surface and dried. Accordingly, the flexible substrate may comprise at least a first major surface that is relatively smooth and free of macrostructure, microstructure, surface roughness, variations in surface wettability, and, in general, any feature or property that might detract from the ability of the chromonic material to form and maintain an oriented structure. The first major surface of the flexible substrate also may exhibit surface properties that allow the flexible substrate to be separated from the layer of dried, oriented chromonic material, over a relatively large area (e.g., at least 20 cm$^2$) without unacceptable damage to the oriented chromonic material. The first major surface of the flexible substrate may comprise surface treatment, coatings, etc., so as to enhance these properties, as desired.

The flexibility of the flexible substrate facilitates the transfer of the oriented chromonic material layer to a receiving substrate, particularly if the transfer is to a curved surface of the receiving substrate. Suitable flexible substrates may include for example films comprised of polyesters such as poly(ethylene terephthalate), poly(ethylene naphthalate), and poly(butylene terephthalate) and copolymers and blends thereof (including oriented versions of such films); polyolefins such as polyethylene, polypropylene, and copolymers and blends thereof (including oriented versions of such films such as biaxially oriented polypropylene film); polyether sulfone; polycarbonate; nylon; polyether ether ketone; polysulfone; polyetherimide; and the like. The second (opposite) major surface of the flexible substrate may be chosen to not unacceptably damage or adhere to the oriented chromonic material upon contacting the oriented chromonic material (e.g., in the event that the flexible substrate with oriented chromonic material thereupon is to be self-wound). Or, a separate protective liner may be applied to the outer-facing surface of the oriented chromonic material layer.

The inventors have found that the dried oriented chromonic material may be physically transferred from the flexible substrate to a receiving substrate, by use of the methods and materials as described herein. In this context, the term "physical transfer" encompasses procedures in which an oriented chromonic material on a flexible substrate, and a receiving substrate, are physically brought together (by moving one or both of the substrates) such that the oriented chromonic material, or a layer thereupon, contacts the receiving substrate, or a layer thereupon, so as to form a laminate structure, after which the flexible substrate is separated from the oriented chromonic material and removed. In this context, a physical transfer process is thus distinguished from other (e.g., thermal) transfer processes.

The physical transfer process disclosed herein is also distinguished from transfer processes that involve a so-called activating step (e.g., a thermal and/or electromagnetic exposure that is designed to weaken the bond between the layer to be transferred and the flexible substrate). Such an activating step may require an additional layer (e.g., of an activating material), and introduce complexity into the transfer process.

The inventors have found that such large-scale physical transfer can be successfully performed in spite of the fact that the oriented chromonic material layer may be fragile with very low cohesive strength (being composed of a material that is not crosslinked and is of relatively low molecular weight, as opposed to being composed of a polymeric material that is crosslinked and/or is strengthened by entangled macromolecules). Such methods and materials make it possible for a relatively large area of oriented chromonic material (e.g., greater than 20 cm$^2$) to be transferred, and in particular make it possible for such a relatively large area of oriented chromonic material to be transferred onto a curved (e.g., a nonplanar, arcuate) surface of a receiving substrate without unacceptable damaging, cracking, etc., of the oriented chromonic material.

In performing such transfer, a molding tool may be used to apply pressure (e.g., from the side of the flexible substrate opposite the oriented chromonic material layer) to physically bring the layers together and to form the laminate structure without damaging the oriented chromonic material. If the receiving surface of the receiving substrate is curved, the contacting surface of the molding tool may be curved to match.

The inventors have found that an oriented chromonic material layer that has been so transferred from a flexible substrate onto a receiving substrate, can be used as an alignment layer in an liquid crystal cell. Such a use requires that the surface of the chromonic material layer that was originally in contact with the flexible substrate (as opposed to the surface that was exposed to air during drying) be used as the alignment surface. Thus, it has been found that the flexible substrate surface, if chosen properly, will not unacceptably prevent the oriented chromonic material molecules that are in contact with this surface during drying, from orienting sufficiently during the drying process. Further, the flexible substrate will separate from the dried, oriented chromonic material layer in such a manner as to not disturb the orientation of the oriented chromonic material molecules, over a relatively large area. These properties in combination allow the use of this transfer method to provide an oriented chromonic material layer that can function as an alignment layer for a liquid crystal cell of relatively large area.

The inventors have discovered that a curable adhesive may be used to facilitate the transfer of the oriented chromonic material layer to a receiving substrate and to bond the oriented chromonic material layer to the receiving substrate (either directly or indirectly, as discussed in detail later herein). If chosen properly, such a curable adhesive can bond to the oriented chromonic material without damaging or disrupting the orientation of the chromonic material. Such a curable adhesive may comprise active groups that can form covalent bonds thus crosslinking, curing and/or hardening the adhesive. In one embodiment, the curable adhesive is relatively flowable in its uncured state, such that it can be contacted with the surface of the oriented chromonic material layer and with another (oppositely-facing) surface of another layer, and can wet out against both surfaces sufficiently that upon curing of the adhesive a bond is established to both surfaces. Thus, in one embodiment, the (uncured) curable adhesive is disposed in a layer such that one major surface of the adhesive layer is in contact with a major surface of the oriented chromonic material, and the other major surface of the adhesive layer is in contact with a major surface of the receiving substrate (or with the surface of an additional layer, e.g. a conductive layer, present on the major surface of the receiving substrate). And, as discussed later herein, it is also possible to provide an additional layer (e.g., a conductive layer) atop the oriented chromonic material such that a surface of this additional layer is what is contacted and bonded by the adhesive, rather than the adhesive bonding directly to the oriented chromonic material layer.

Once the curable adhesive is in contact with the two layers that are desired to be bonded together, the adhesive is cured. Such curing may occur by the application of an activating treatment (which may be heat, radiation, etc, e.g., in the case of photocurable adhesives.). Or, the curing process may be activated by the presence of adventitious substances present on one of the layers to be bonded (e.g., in the case of cyanoacrylate adhesives). Or, if the adhesive is for example a two-part adhesive which is mixed prior to application, the adhesive may be allowed to cure over time (possibly aided by elevated temperature). Thus in general, suitable adhesives for use in this application may include photocurable adhesives, two-part epoxy adhesives, cyanoacrylate adhesives, and the like.

The adhesive is cured so as to permanently bond the oriented chromonic material to the receiving substrate, or to permanently bond the oriented chromonic material to an intermediate layer present on the receiving substrate. In doing so, the adhesive may form at least some covalent bonds with the surface of either of the layers being bonded, e.g., with molecules of the oriented chromonic material.

In some embodiments, the curable adhesive may be deposited onto a receiving substrate, with the oriented chromonic material layer then being contacted with the adhesive layer and the adhesive then cured. In alternative embodiments, the curable adhesive may be deposited onto the (dried) oriented chromonic material layer, with the receiving substrate then being contacted with the adhesive layer and the adhesive then cured.

In specific embodiments, the curable adhesive is chosen so as to provide a relatively hard and rigid network once cured. Such a property can decrease the likelihood of the oriented chromonic material being damaged, cracked, deformed, etc. upon further handling (e.g., upon assembly into a liquid crystal cell), and/or upon exposure to heat. In various embodiments, the curable adhesive comprises, once cured, a Shore D hardness value (as measured, for example, according to the method outlined in ASTM D2240-05) of at least about 20, at least about 40, or at least about 60.

In particular embodiments, the curable adhesive does not comprise, either before or after being cured, a pressure-sensitive adhesive as commonly known (e.g., as described in U.S. Pat. No. 7,026,168, column 16 lines 11-40, incorporated by reference herein for this purpose).

In certain embodiments, the curable adhesive is optically clear (thus rendering it particularly suitable for use in optical devices such as liquid crystal cells).

In summary, curable adhesives that may be used include any that are sufficiently flowable when uncured, are curable to a sufficiently rigid state, and that are sufficiently optically clear when cured. Specific adhesives which may be used include for example the product available from 3M Company of St. Paul, Minn., under the trade designation CA8 Instant Adhesive, the product available from Norland Products of Cranbury, N.J., under the trade designation Optical Adhesive 68, and the product available from Delo Industrial Adhesive Company, Windach, Germany, under the trade designation Delo Katiobond 698.

The oriented chromonic material described herein may be transferred from a flexible substrate onto a receiving substrate, and the flexible substrate removed, in order to form a subassembly which may find use e.g. in assembly of a liquid crystal cell. Suitable receiving substrates may include any optically clear material. With reference to materials disclosed herein, a material is considered optically clear if it is capable of permitting the passage of at least an appreciable amount of light. Preferably, the optically clear material permits the passage of substantial amounts of (visible) light, and, most preferably, may be characterized as transparent. Exemplary optically clear materials may include, for example film (e.g., of thickness around 1.0 mm or less) comprised of polyesters such as poly(ethylene terephthalate), poly(ethylene naphthalate), and poly(butylene terephthalate) and copolymers and blends thereof (including oriented versions of such films); polyolefins such as polyethylene, polypropylene, and copolymers and blends thereof (including oriented versions of such films such as biaxially oriented polypropylene film); polycyclic olefins, polyarylates, polyether sulfone; polycarbonate; nylon; polyether ether ketone; polysulfone; polyetherimide; and the like. In certain embodiments, which may be particularly useful in applications such as autodarkening filters (e.g. for eye protection in welding operations), receiving substrates may be chosen to have enhanced resistance to heat. Such receiving substrates may be comprised of organic polymeric (e.g., thermoplastic or thermoset) materials that are chosen to have enhanced thermal properties (e.g., certain polycarbonates, polysulfone, polyether ether ketone, polyarylate, polycyclic olefins, etc.). In a particular embodiment, the receiving substrate comprises (silica-based) glass.

In some embodiments, the receiving substrate may be flexible (e.g., comprised of a flexible organic polymeric (thermoplastic or thermoset) such as those listed above). Such flexible receiving substrates may be particularly useful in certain embodiments, as discussed later herein.

The receiving substrate comprises at least a first major (receiving) surface that is capable of receiving the oriented chromonic material (or of receiving any intermediate layer such as a conductive layer, adhesive layer, etc.). In further embodiments, the first major surface of the receiving substrate is a curved major surface. In specific embodiments, the curved major surface is a concave major surface or a convex major surface. The receiving substrate may also comprise an oppositely-facing (relative to the first major surface) second major surface. The second major surface may be curved and if so may generally match the curvature of the first major surface (e.g., the first major surface may comprise a concave curvature and the second major surface may comprise a convex curvature that generally parallels the curvature of the first major surface). Such arrangements may be achieved by providing the receiving substrate with such curvature (e.g., by molding a substrate in the desired shape, by grinding the surfaces of a substrate in the desired shape), or by bending a flexible substrate to the desired curvature.

In some embodiments, the receiving substrate may comprise relatively thick sheeting (e.g., of thickness 1 mm or greater) or slab, rather than the above-described film (in such case the receiving substrate can be comprised of any of the above-listed materials). In certain embodiments of this type, the sheeting or slab can comprise one major surface (e.g., a receiving surface) that is curved and another, oppositely-facing, surface that is generally flat and/or is not curved in the same shape or manner as is the first (receiving) surface.

Liquid crystal cells typically include at least one optically clear conductive layer (e.g., indium tin oxide). Often, such conductive materials are vapor deposited (e.g., by sputter coating, chemical vapor deposition, etc.). In some embodiments, such a conductive layer is deposited on a receiving substrate (for example, on the concave major surface of an optically clear substrate). A curable adhesive is then deposited atop the conductive layer, after which an oriented chromonic material layer (on a flexible substrate) is contacted with the adhesive layer and the adhesive cured. In alternative embodiments, a conductive layer is deposited on a receiving substrate, a curable adhesive is deposited on an oriented chromonic material layer (on a flexible substrate), after which the receiving substrate with conductive layer thereon is then contacted with the adhesive and the adhesive cured. In either case, the cured adhesive serves to bond the oriented chromonic material layer to the conductive layer.

In still other embodiments, a conductive layer may be deposited (for example, vapor deposited) directly onto the surface of a dried oriented chromonic material layer. The inventors have found that the integrity of the oriented chromonic material layer and of the conductive layer thereupon, and the bond between the two, can be maintained during assembly of a liquid crystal cell. This enables a production method in which an oriented chromonic material layer is deposited atop a flexible substrate, after which a conductive layer is deposited atop the oriented chromonic material, after which a curable adhesive is used to bond the conductive layer to the receiving substrate. In some embodiments, a curable adhesive is deposited on a receiving substrate, and a conductive layer/oriented chromonic material layer/flexible substrate stack brought together with the curable adhesive/receiving substrate stack such that the conductive layer contacts the adhesive and the adhesive bonds the conductive layer and the receiving substrate upon curing of the adhesive. In alternative embodiments, a curable adhesive is deposited on the conductive layer of a conductive layer/oriented chromonic material layer/flexible substrate stack, and this stack is brought together with a receiving substrate such that the adhesive contacts the receiving substrate and the adhesive bonds the conductive layer and the receiving substrate upon curing of the adhesive.

Thus, methods disclosed herein include those discussed below with reference to FIGS. 1-4:

In a first embodiment illustrated in exemplary fashion in FIG. 1, an oriented chromonic material layer 400 is provided (e.g., by coating and drying) on flexible substrate 600, a conductive layer 200 is deposited upon major surface 110 of receiving substrate 100 (which may be a concave major surface, as in the exemplary illustration of FIG. 1), and a layer of curable adhesive 300 is deposited upon conductive layer 200. The oriented chromonic material layer 400/flexible substrate 600 stack and the receiving substrate 100/conductive layer 200/adhesive layer 300 stack are brought together such that curable adhesive layer 300 contacts oriented chromonic material layer 400. Adhesive layer 300 is then cured to form cured adhesive layer 310 (not shown in FIG. 1), after which flexible substrate 600 is separated from oriented chromonic material layer 400 and removed, thus providing a subassembly (which may thereafter be assembled, e.g., into a liquid crystal cell).

Figure 2:
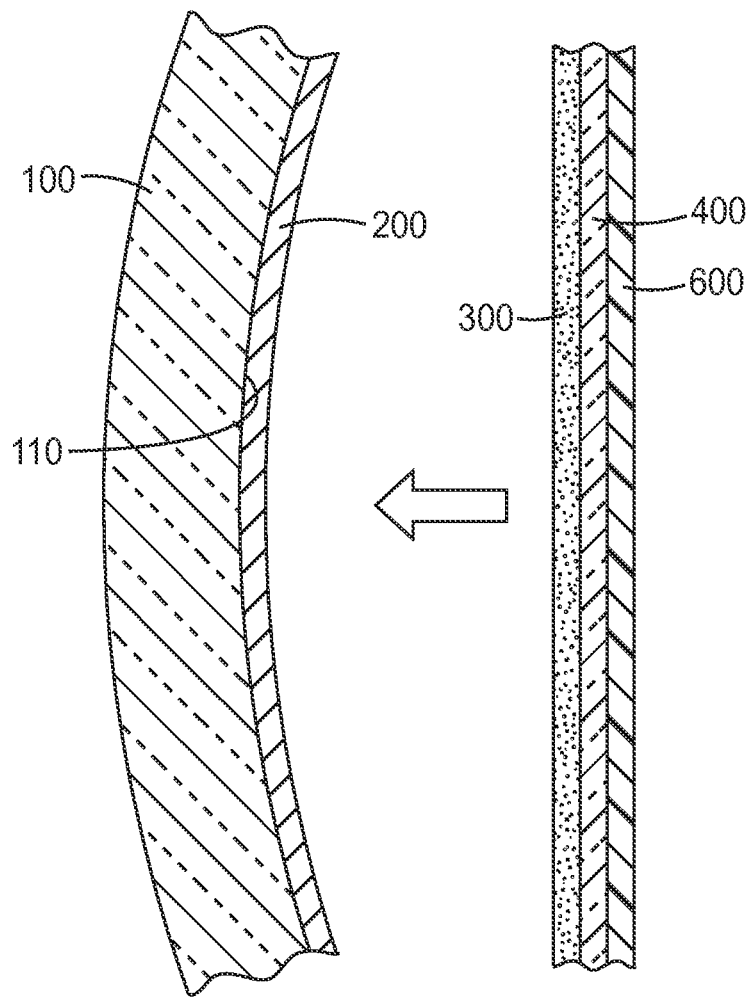
FIG. 2 is a side schematic cross sectional view illustrating an exemplary method disclosed herein.

In a second embodiment illustrated in exemplary fashion in FIG. 2, an oriented chromonic material layer 400 is provided on flexible substrate 600, a layer of curable adhesive 300 is deposited upon oriented chromonic material layer 400, and a conductive layer 200 is deposited upon major surface 110 of receiving substrate 100 (which may be a concave major surface, as in the exemplary illustration of FIG. 2). The adhesive layer 300/oriented chromonic material layer 400/flexible substrate 600 stack and the receiving substrate 100/conductive layer 200 stack are then brought together such that curable adhesive layer 300 contacts conductive layer 200. Adhesive layer 300 is then cured to form cured adhesive layer 310, after which flexible substrate 600 is separated from oriented chromonic material layer 400 and removed.

Figure 3:
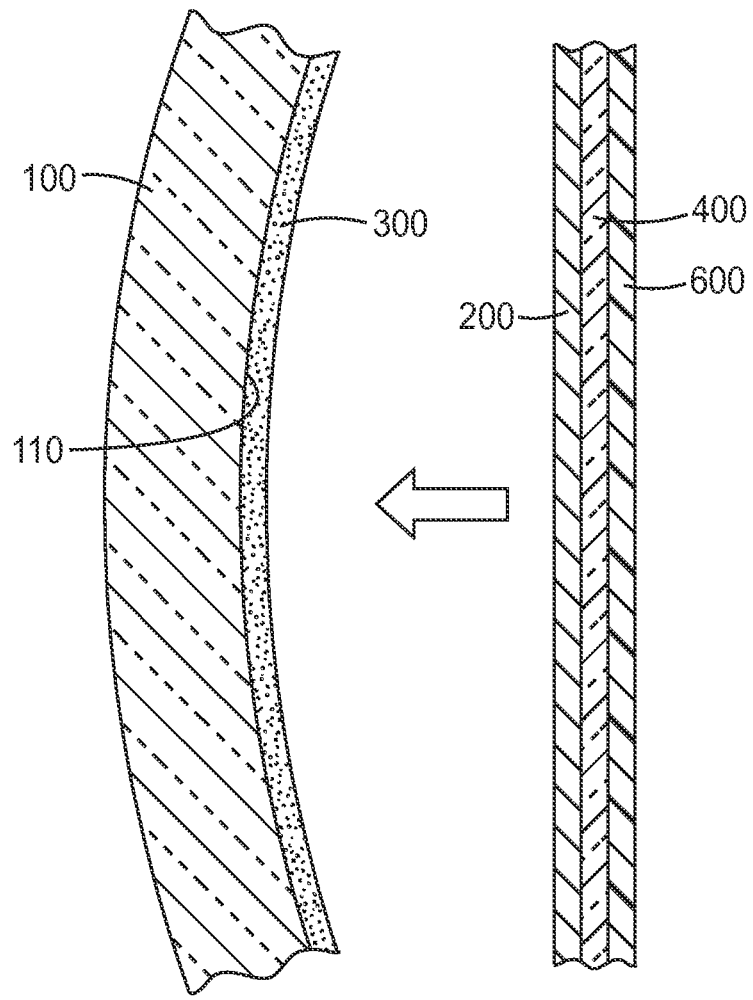
FIG. 3 is a side schematic cross sectional view illustrating an exemplary method disclosed herein.

In a third embodiment illustrated in exemplary fashion in FIG. 3, an oriented chromonic material layer 400 is provided on flexible substrate 600, a conductive layer 200 is deposited upon oriented chromonic material layer 400, and a layer of curable adhesive 300 is deposited upon major surface 110 of receiving substrate 100 (which may be a concave major surface, as in the exemplary illustration of FIG. 3). The conductive layer 200/oriented chromonic material layer 400/flexible substrate 600 stack and the receiving substrate 100/adhesive layer 300 stack are then brought together such that curable adhesive layer 300 contacts conductive layer 200. Adhesive layer 300 is then cured to form cured adhesive layer 310, after which flexible substrate 600 is separated from oriented chromonic material layer 400 and removed.

Figure 4:
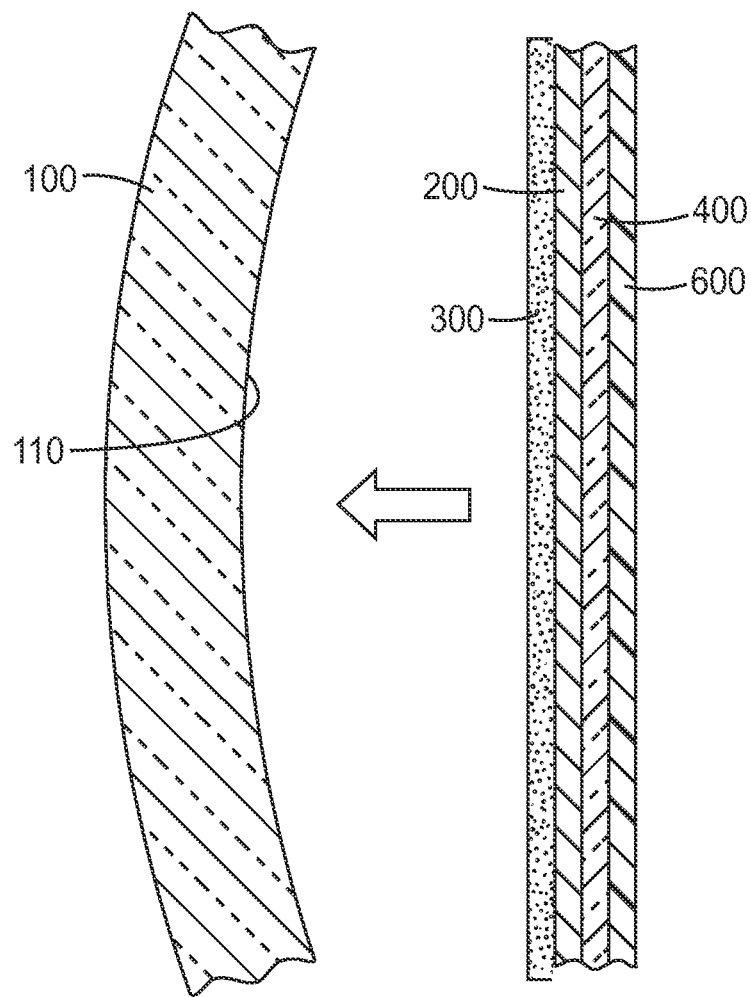
FIG. 4 is a side schematic cross sectional view illustrating an exemplary method disclosed herein.

In a fourth embodiment illustrated in exemplary fashion in FIG. 4, an oriented chromonic material layer 400 is provided on flexible substrate 600, a conductive layer 200 is deposited upon oriented chromonic material layer 400, and a layer of curable adhesive 300 is deposited upon conductive layer 200. Receiving substrate 100 comprising major surface 110 (which may comprise a concave major surface, as in the exemplary illustration of FIG. 4) is then provided. The adhesive layer 300/conductive layer 200/oriented chromonic material layer 400/flexible substrate 600 stack and receiving substrate 100 are then brought together such that curable adhesive layer 300 contacts major surface 110 of receiving substrate 100. Adhesive layer 300 is then cured to form cured adhesive layer 310, after which flexible substrate 600 is separated from oriented chromonic material layer 400 and removed.

Figure 5:
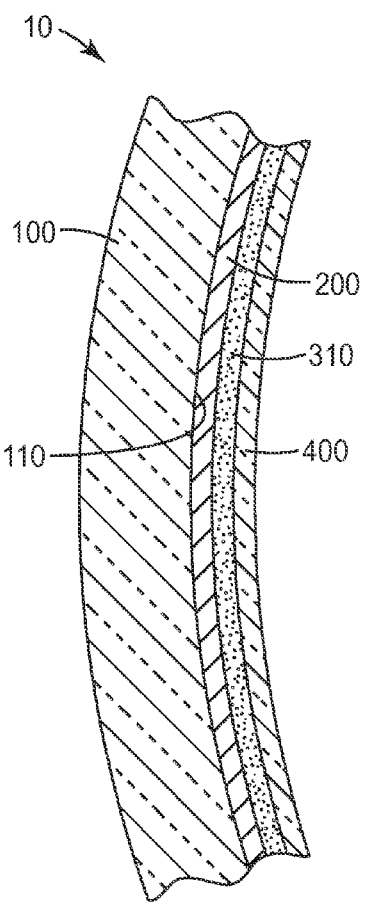
FIG. 5 is a side schematic cross sectional view illustrating an exemplary subassembly disclosed herein.
Figure 6:
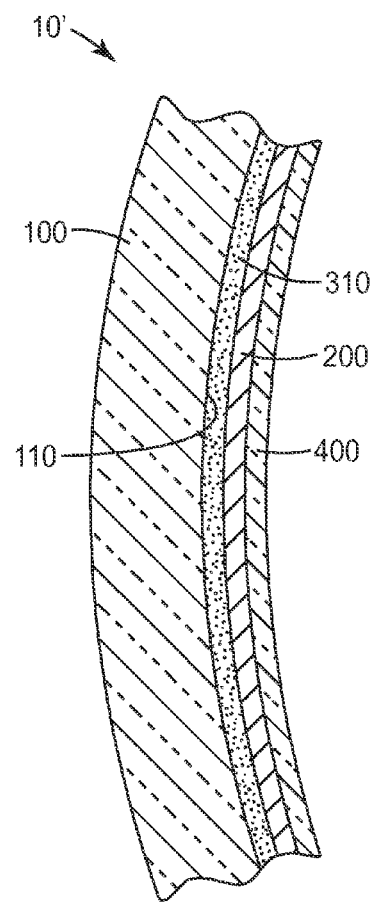
FIG. 6 is a side schematic cross sectional view illustrating an exemplary subassembly disclosed herein.

The processes described above with reference to FIGS. 1-4 may be used to produce subassembly 10/10', illustrated in alternative embodiments in FIGS. 5 and 6. Subassembly 10/10' may then be used in the production of a liquid crystal cell assembly. In the embodiment of FIG. 5 (made by the procedures described with reference to FIG. 1 or 2), subassembly 10 comprises in order receiving substrate 100, conductive layer 200, cured adhesive layer 310, and oriented chromonic material layer 400. In the embodiment of FIG. 6 (made by the procedures described with reference to FIG. 3 or 4), subassembly 10' comprises in order receiving substrate 100, cured adhesive layer 310, conductive layer 200, and oriented chromonic material layer 400.

In various embodiments, the processes described above with reference to FIGS. 1-4 may be performed with the area of oriented chromonic material layer 400 being relatively large, such that the area of subassembly 10/10' thus formed is relatively large. In a various embodiments, oriented chromonic material layer 400 that is transferred from flexible substrate 600 comprises at least 20 cm$^2$, at least 30 cm$^2$, or at least 50 cm$^2$, in area. In further embodiments, the processes described above with reference to FIGS. 1-4 may be carried out such that the area of oriented chromonic material layer 400 that is transferred to major surface 110 of receiving substrate 100 is of a similar size to the area of major surface 110. In various embodiments, the area of oriented chromonic material layer 400 that is transferred to major surface 110 of receiving substrate 100 is at least about 70%, at least about 80% or at least about 90%, of the area of major surface 110.

In further embodiments, the processes described with reference to FIGS. 1-4 may be performed wherein major surface 110 of receiving substrate 100 is curved (either concave or convex). In such a case, oriented chromonic material layer 400 is transferred to curved major surface 110 of receiving substrate 100 in a manner such that little or no shear stress is applied to the oriented chromonic material, so that oriented chromonic material layer 400 retains its integrity (e.g., does not crack, fracture, etc.) during this process. In specific embodiments, curved major surface of 110 receiving substrate 100 comprises a concave major surface.

In still further embodiments of the processes described with reference to FIGS. 1-4, receiving substrate 100 comprises a concave major surface 110 with a radius of curvature of between 40 mm and 200 mm. Such radii of curvature may render subassembly 10/10' useful in a relatively large and curved liquid crystal cell that, as part of a personal protective device, may afford improved visibility for a user. Different devices may be produced with different radii of curvature, for example to provide personal protective equipment of different sizes.

Subassembly 10/10' as disclosed herein, produced as described above with reference to FIGS. 1-4, may find use in the formation of a liquid crystal cell assembly. To form such a liquid crystal cell, a second subassembly may be provided. Such a subassembly may comprise at least a second substrate (e.g., a glass substrate), conductive layer, and alignment layer. The alignment layer may comprise an oriented chromonic material layer as described above; or, a conventional alignment layer (e.g., a rubbed polyimide film) may be used. The second subassembly may also comprise a polarizer (for example, a polarizer that is oriented at a desired angle, e.g., a right angle, versus the polarizing layer of the first subassembly, as is well known in the art). Various other layers may be provided as desired in either subassembly, as desired.

In embodiments in which oriented chromonic material layer 400 and the above-described associated layers are deposited onto a concave major surface 110 of receiving substrate 100 to form subassembly 10/10' (e.g., as in FIGS. 1-6), the second substrate (in the second subassembly) may be chosen to have a convex major surface that preferably closely matches the size and curvature of concave major surface 110 of receiving substrate 100 (such a design allows the two substrates to be mated to form a curved liquid crystal cell, as discussed later herein).

To form a liquid crystal cell, the second subassembly is mated to first subassembly 10/10' (e.g., the two subassemblies are brought into close proximity with each other) so as to form a relatively narrow cavity (e.g., less than about 100 microns, often about 2-10 microns, in width) therebetween, with the alignment layer of first subassembly 10/10' and the alignment layer of the second subassembly in close proximity and facing each other with a narrow cavity therebetween. In particular embodiments, the two subassemblies are designed and mated such that the width (between the two alignment layers) of the narrow cavity therebetween is relatively constant over, e.g., about 80 percent of the area of first subassembly 10/10' (such a generally uniform, e.g. within plus or minus 50%, cavity width may be achieved e.g. by the use of spacing elements such as glass microspheres of relatively uniform diameter, as is known in the art). Liquid crystal material is then inserted into the cavity so as to fill the cavity and contact both of the oppositely-facing alignment layers. The perimeter of the assembly may be sealed by methods known in the art, conductive leads connected to the conductive layers of the assembly, and so on, in order to provide a fully functional liquid crystal cell.

Figure 7:
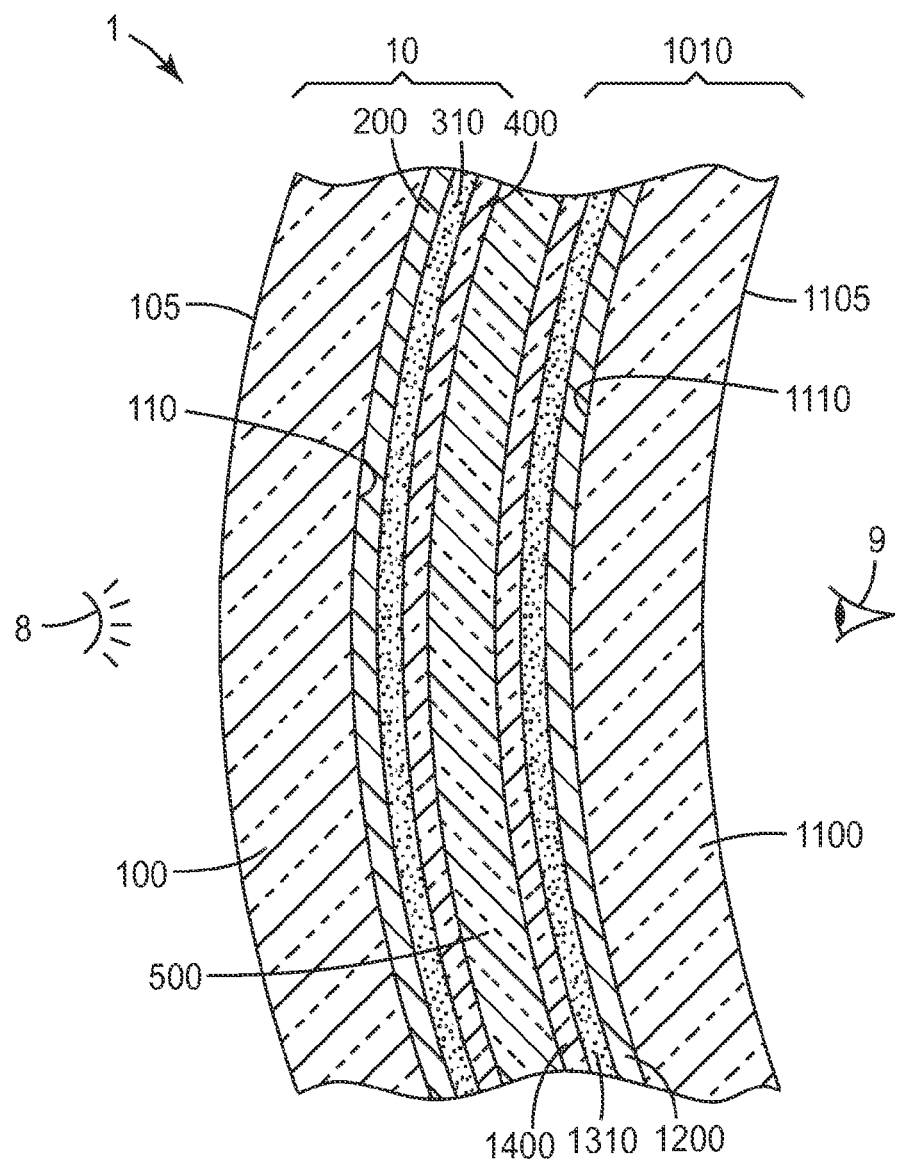
FIG. 7 is a side schematic cross sectional view illustrating an exemplary liquid crystal cell.

An embodiment of a liquid crystal cell made by methods described herein is illustrated in an exemplary manner in FIG. 7, and may be produced as follows: first subassembly 10 as pictured in FIG. 5 is produced (e.g., by the process described above with respect to FIG. 1 or FIG. 2), comprising receiving substrate 100 with concave major surface 110, on concave major surface 110 there being, in order, conductive layer 200, cured adhesive layer 310, and oriented chromonic material layer 400. A second subassembly 1010 is provided, made by similar processes as described above, comprising second substrate 1100 with convex major surface 1110, on convex major surface 1110 there being, in order, conductive layer 1200, cured adhesive layer 1310, and oriented chromonic material layer 1400. The two subassemblies are mated together so as to provide a narrow cavity between oriented chromonic material layer 400 and oriented chromonic material layer 1400. Liquid crystal material is then inserted into the cavity so as to provide liquid crystal layer 500, in direct contact with oriented chromonic material layers 400 and 1400.

Figure 8:
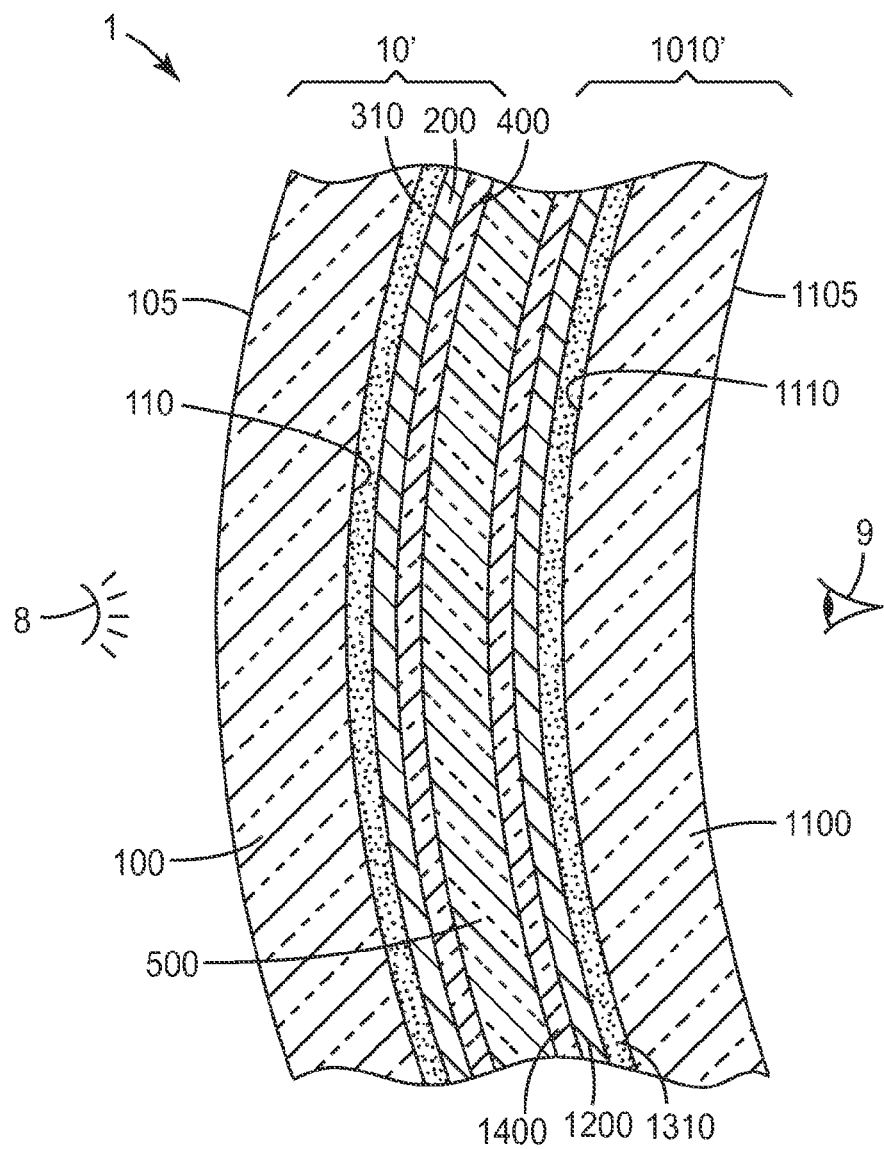
FIG. 8 is a side schematic cross sectional view illustrating an exemplary liquid crystal cell.

Another embodiment of a liquid crystal cell made by methods described herein is illustrated in an exemplary manner in FIG. 8, and may be produced as follows: first subassembly 10' as pictured in FIG. 6 is produced (e.g., by the process described above with respect to FIG. 3 or FIG. 4) comprising receiving substrate 100 with concave major surface 110, on concave major surface 110 there being, in order, cured adhesive layer 310, conductive layer 200, and oriented chromonic material layer 400. A second subassembly 1010' is provided, made by similar processes as described above, comprising a second substrate 1100 with a convex major surface 1110, on convex major surface 1110 there being, in order, cured adhesive layer 1310, conductive layer 1200, and oriented chromonic material layer 1400. The two subassemblies are mated so as to provide a narrow cavity between oriented chromonic material layer 400 and oriented chromonic material layer 1400. Liquid crystal material is then inserted into the cavity so as to provide liquid crystal layer 500, in direct contact with oriented chromonic material layers 400 and 1400.

In the above disclosures, the various coatings are typically applied to the surfaces of the receiving substrates, and subassemblies are assembled, such that the various layers (chromonic material layers, conductive layers, adhesive layers, etc.) are coextensive, e.g., all in overlapping relation with each other, at least within the area of the desired optical pathway. This optical pathway may correspond to the desired viewing area of the finished liquid crystal cell and/or of an automatic darkening filter to be made from such a liquid crystal cell, and may have an area of, for example, at least 20 $cm^2$, at least 30 $cm^2$, or at least 50 $cm^2$.

In other embodiments (not shown in any Figure), a first subassembly of type 10 may be mated with a second subassembly of type 1010'; or, a first subassembly of type 10' may be mated with a second subassembly of type 1010.

As mentioned above, rather than using a second subassembly of type 1010 or 1010', the second subassembly may use a conventional alignment layer rather than oriented chromonic material layer 1400, and/or may use a conventional polarizer rather than including a pleochroic dye in oriented chromonic material layer 1400 (in such a case oriented chromonic material layer 1400 may be present but not contain a pleochroic dye, or oriented chromonic material layer 1400 may be absent). Such a conventional polarizer may be located on the front or back side of second substrate 1100.

In liquid crystal cells as disclosed herein, the polarizing layers and the alignment layers may be configured (e.g., oriented relative to each other) so as to provide a liquid crystal cell with a desired twist angle, as known in the art. A liquid crystal cell may be provided that is more transmissive to light upon application of electric power to the cell, or that is less transmissive to light upon application of electric power, again as is known in the art.

Other designs and arrangements are contemplated by the inventors. For example, at least one of receiving substrate 100 or 1100 may be flexible, as mentioned previously. In embodiments of this type, subassembly 10/10' may be flat as assembled (rather than curved as shown in the exemplary embodiments of FIGS. 5 and 6) and may be curved after assembly, to a desired shape for example to allow it to be mated to a curved secondary assembly 1010/1010'. Likewise, secondary assembly 1010/1010' may be flat as assembled and may be curved thereafter to a desired shape for mating to a curved assembly 10/10'. In specific embodiments, both subassembly 10/10' and secondary subassembly 1010/1010' may be flexible, such that liquid crystal cell 1 formed from the combination thereof is flat. Liquid crystal cell 1 may then be curved after assembly (e.g., to a shape similar to that shown in FIGS. 7 and 8).

In certain embodiments, rather than being produced by transfer of layers from a flexible substrate, layers (e.g., chromonic layers, conductive layers, etc.) may be coated directly onto a receiving substrate, e.g., a flat, flexible receiving substrate, which may then be curved (e.g., as part of a subassembly or as part of a liquid crystal cell) in the formation of a curved liquid crystal cell.

Liquid crystal cells made as described herein may possess several advantages. As mentioned earlier, the inclusion of a pleochroic dye in oriented chromonic material layer 400 may allow oriented chromonic material layer 400 to be used not only as an alignment layer but also as a polarizing layer. The need for a separate conventional polarizer may thus be avoided. (If a second oriented chromonic material layer 1400 is present and includes a pleochroic dye, then an additional conventional polarizer may be avoided). Also, in the specific embodiment in which conductive layer 200 is deposited directly on oriented chromonic material layer 400 (e.g., as shown in FIG. 3, so as to provide subassembly 10' in the configuration illustrated in FIG. 6), the distance between conductive layer 200 and conductive layer 1200 may be minimized (since in this embodiment cured adhesive layer 310 is not located between conductive layers 200 and 1200). Similarly, if conductive layer 1200 is deposited directly on oriented chromonic material layer 1400, the distance between conductive layer 200 and conductive layer 1200 may be further minimized (since in this embodiment cured adhesive layer 1310 is not located between conductive layers 200 and 1200). This minimization of the distance between conductive layers 200 and 1200 (e.g., as illustrated in FIG. 8) may advantageously minimize the amount of voltage needed to operate the liquid crystal cell.

The above-described designs may be particularly advantageous in the case in which the liquid crystal cell is used in an autodarkening filter. In the exemplary designs of FIGS. 7 and 8, no components (e.g., conductive layer, polarizing layer, alignment layer) are located on the "outside" of first substrate 100 (that is, on the side of first substrate 100 closest to light/heat source 8). Specifically, liquid crystal cell 1 of FIGS. 7 and 8 comprises an "internal" polarizer (e.g. combined alignment/polarizing layer 400), meaning that polarizing layer 400 is located between substrates 100 and 1100, as opposed to an "external" polarizer which would be located on the outside of substrate 100 (i.e., toward external light source 8). The methods presented herein thus may advantageously allow certain layers to be placed on the opposite side of substrate 100 (which, as mentioned above, may be chosen so as to comprise enhanced heat resistance) from external light/heat source 8.

Figure 9:
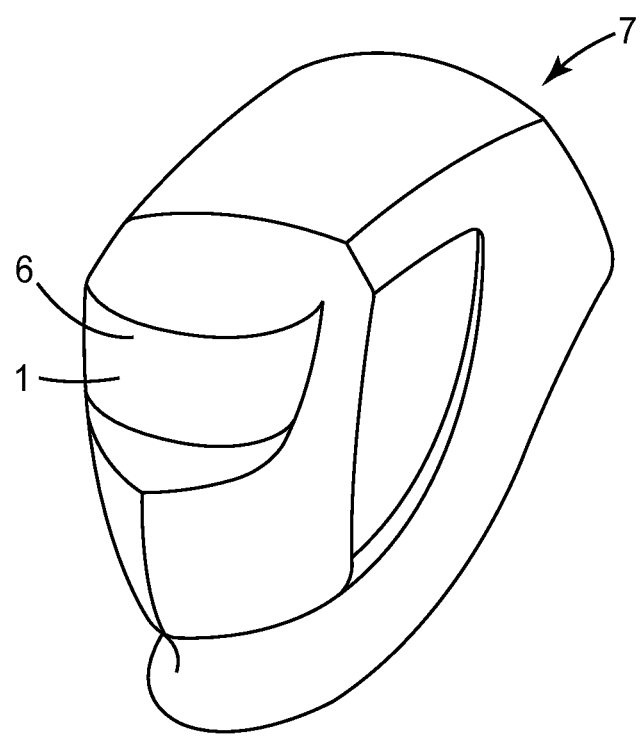
FIG. 9 is a perspective view illustrating an exemplary personal protection device comprising an autodarkening filter that comprises at least one liquid crystal cell.

Embodiments in which substrate 100 of liquid crystal cell 1 comprises concave major surface 110 (either by use of a substrate 100 that comprises concave major surface 110 as provided, or by the use of a flexible substrate 100 such subassembly 10/10' and/or liquid crystal cell 1 may be curved after assembly thereof so as to provide the desired concavity of surface 110) may be particularly advantageous for the production of an autodarkening filter for an eye protection apparatus. As mentioned, such an arrangement allows a curved (arcuate) autodarkening filter to be produced. The use of such an arcuate autodarkening filter is shown in exemplary manner in FIG. 9, which portrays welding helmet 7 comprising curved autodarkening filter 6 which comprises curved liquid crystal cell 1. Thus, liquid crystal cell 1 may be a part of autodarkening filter 6 which is arranged such that, when an eye protection apparatus (e.g., helmet 7) is worn by a user, concave major surface 110 of first substrate 100 faces inward toward the eyes of the user and second, oppositely facing major surface 105 of first substrate 100 faces outward toward light/heat source 8. As mentioned, the use of a curved autodarkening filter may allow a wider field of vision, a more distortion-free field of vision, and/or a more continuous, uninterrupted field of vision, than an autodarkening filter that uses a single flat liquid crystal cell or an array of several flat liquid crystal cells. In various embodiments, the viewing area of autodarkening filter 6/liquid crystal cell 1 may be as large as at least 20 $cm^2$, at least 30 $cm^2$, or at least 50 $cm^2$.

In the formation of liquid crystal cells and/or autodarkening filters and/or personal protective equipment using the methods presented herein, numerous variations are possible. For example, an autodarkening filter 6 incorporating liquid crystal cell 1 as disclosed herein may also use additional liquid crystal cells in the same optical pathway, which may be conventional liquid crystal cells or may rely at least partially on the methods and devices disclosed herein. Other layers (e.g., I filters, UV filters, etc.) may also be present. Also, while in the various figures shown herein oppositely-facing major surface 105 of first substrate 100 (i.e., oppositely facing from major surface 110) has been shown for purposes of illustration as convex and closely matching (paralleling) the curvature of concave major surface 110, this is not required. For example, opposite-facing surface 105 could comprise a single flat surface, could comprise multiple flat surfaces, etc. Likewise, while opposite side 1105 of second substrate 1100 is shown (e.g. in FIG. 7) as being concave and closely matching convex major surface 1110 of substrate 1100, this also is not required.

In some embodiments in the use of liquid crystal cell 1 in the production of an autodarkening filter 6, liquid crystal 1 may be positioned behind one or more layers that comprise any or all of enhanced heat resistance, enhanced resistance to penetration by water, moisture, organic vapors, etc. (In particular embodiments, the entirety of liquid crystal cell 1 may be substantially or completely sealed within a chamber comprised of materials with enhanced resistance to heat, water, moisture, organic vapors, etc.) Such arrangements may be particularly suitable for example in cases in which certain components of liquid crystal cell 1 are not chosen to be particularly heat-resistant (e.g., in cases in which substrates 100 and/or 1100 are comprised of e.g. thermoplastic materials such as polypropylene, poly(ethylene terephthalate) etc.

In further embodiments, substrate 100 may comprise compound curvature. That is, instead of comprising an arcuate shape with a single, relatively constant radius of curvature, substrate 100 may comprise a design in which the radius of curvature differs over major surface 110 of substrate 100. (Substrate 1100 may be similarly designed, e.g. to match the shape of substrate 100). Such an arrangement may allow the production of an autodarkening filter with further enhanced field of vision, e.g. that wraps around the eyes of a user so as to provide improved peripheral vision.

Example 4-dimethylamino-1-[4,6-di(4-carboxyphenylamino)-1,3,5-triazin-2-yl]pyridium chloride (a chromonic material corresponding to Formula III as disclosed herein), was prepared in similar manner as described Example 1 of U.S. Pat. No. 6,488,866.

A mixture was then prepared of the following ingredients: approximately 5.0 grams deionized water, approximately 1.0 g of the above chromonic material, approximately 3.5 grams of a 9 wt. % aqueous solution of Direct Blue 199 (available from Sensient Technologies, Milwaukee, Wis.), approximately 0.2 gram of ethylene diamine (available from Sigma-Aldrich of St. Louis, Mo.), approximately 0.25 gram of Direct Red 79 (>95% pure) available from Sensient Corporation), approximately 0.25 gram of Reactive Yellow 27 (available from Sensient Corporation), and approximately 0.045 gram of a 10 wt. % aqueous solution of Triton X-100 (available from Sigma Aldrich).

The above materials were stirred together until they appeared to be completely dissolved, after which the solution was filtered in a 5 μm syringe filter. The solution was then shear coated using a laboratory knife coater on a poly(ethylene terephthalate) (PET) film (available under the trade designation Mylar from DuPont Teijin Films U.S. Limited Partnership of Hopewell, Va.), having a thickness of approximately 0.125 mm. The wet coating thickness of the coating solution was selected so as to provide a nominal thickness of the chromonic material after drying in the range of 1-2 microns. The coating was air dried for at least 15 minutes, after which a thin layer of indium tin oxide was sputter coated atop the dried chromonic coating. (The indium tin oxide coating was applied at a thickness (approximately a few hundred angstroms) aimed at providing a conductive coating with nominal resistivity in the range of a few hundred ohms). A flexible stack was thus provided comprising the polyester substrate, dried chromonic material, and indium tin oxide.

A curved glass substrate was obtained having a thickness of approximately 3 mm, a width of approximately 50 mm, a length of approximately 140 mm, and a radius of curvature of approximately 114 mm. A layer of UV curable adhesive (Optical Adhesive 68, available from Norland Products of Cranbury, N.J.) was coated onto the concave surface of the glass substrate at a thickness of approximately 5 micron.

The flexible stack was then gently laminated using a rubber roller (with the indium tin oxide comprising the convex outermost surface of the stack) to the concave side of the glass substrate so that the indium tin oxide contacted with the UV curable adhesive. The stack was held in this position and the adhesive was cured by the application of UV light using a 365 nm UV lamp (from Sigma-Aldrich Corp) for approximately 3 minutes. The polyester substrate was then removed leaving the glass substrate with cured adhesive, indium tin oxide, and dried chromonic material, thereupon.

The tests and test results described above are intended solely to be illustrative, rather than predictive, and variations in the testing procedure can be expected to yield different results. The foregoing detailed description and examples have been given for clarity of understanding only. No unnecessary limitations are to be understood therefrom.

The present invention has now been described with reference to several embodiments thereof. It will be apparent to those skilled in the art that changes can be made in the embodiments described without departing from the scope of the invention. Thus, the scope of the present invention should not be limited to the exact details and structures described herein, but rather by the structures described by the language of the claims, and the equivalents of those structures.

What is claimed is:

1. An optical control device comprising:
  an optically clear first substrate comprising at least a curved first major surface;
  a conductive layer adjacent the curved first major surface of the first substrate;
  an alignment-polarizer layer adjacent the conductive layer, wherein the alignment-polarizer layer comprises an oriented chromonic material that further comprises at least one pleochroic dye;
  an optically clear second substrate comprising at least a curved first major surface,
    wherein the curved first major surface of the first substrate, and the curved first major surface of the second substrate, are mated so as to define a cavity therebetween; and,
  a liquid crystal material layer between the alignment-polarizer layer and the curved first major surface of the second substrate and the liquid crystal material layer being in contact with the alignment-polarizer layer;
    wherein the conductive layer is disposed on the curved first major surface of the first substrate and wherein the alignment-polarizer layer is bonded to the conductive layer by a layer of cured optically clear adhesive therebetween, and wherein the optically clear first substrate is a glass substrate and wherein the optical control device is a curved autodarkening filter of an eye protection apparatus.

2. The device of claim 1 wherein the optically clear first substrate comprises an oppositely-facing second major surface and wherein the optical control device is a part of the eye protection apparatus that is arranged such that, when the apparatus is worn by a user, the curved first major surface of the first substrate faces inward toward the eyes of the user and the second major surface of the first substrate faces outward away from the eyes of the user.

3. The device of claim 1 wherein the curved first major surface of the first substrate, the conductive layer, and the alignment-polarizer layer, comprise at least a coextensive area of at least 20 cm$^2$.

4. The device of claim 3 wherein the curved first major surface of the first substrate is a concave surface comprising a radius of curvature of between 40 and 200 mm.

5. The device of claim 4 wherein the concave first major surface of the first substrate and the curved first major surface of the second substrate are mated so as to provide a cavity therebetween that is generally uniform in thickness over at least 80 percent of the area of the concave first major surface of the first substrate.

6. The device of claim 4 wherein the first substrate comprises differing radii of curvature over the concave first major surface of the first substrate.

7. The device of claim 1 wherein the second substrate comprises an oppositely-facing second major surface and wherein the device further comprises a second conductive layer adjacent the curved first major surface of the second substrate, and an alignment layer adjacent the second conductive layer and in contact with the liquid crystal material layer, and a polarizer layer adjacent the curved first major surface of the second substrate or the oppositely-facing second major surface of the second substrate.

8. The device of claim 7 wherein the alignment layer adjacent the second conductive layer, and the polarizer layer adjacent the curved first major surface of the second substrate or the oppositely-facing second major surface of the second substrate, comprise a single second alignment-polarizing layer that is between the second conductive layer and the liquid crystal material layer and that is in contact with the liquid crystal material layer, and wherein the single second alignment-polarizer layer comprises an oriented chromonic material comprising at least one pleochroic dye.

9. The device of claim 8 further comprising a layer of cured optically clear adhesive between the single second alignment-polarizer layer and the curved first major surface of the second substrate.

10. The device of claim 1 wherein the autodarkening filter comprises an optical pathway that provides a viewing area for a wearer of the eye protection apparatus and wherein the conductive layer, the alignment-polarizer layer, the liquid crystal material layer, and the cured optically clear adhesive layer are all coextensive with each other at least within the viewing area of the autodarkening filter.

11. The device of claim 1 wherein the eye protection apparatus is part of a welding helmet.

12. The device of claim 1 wherein the device further comprises an ultraviolet radiation filter layer.

13. The device of claim 1 wherein the optically clear first substrate is glass sheeting with a thickness of about 1 mm or greater.

14. The device of claim 1 wherein the cured optically clear adhesive is a hard and rigid network with a Shore D hardness of at least about 40.

15. The device of claim 1 wherein the cured optically clear adhesive is not a pressure-sensitive adhesive.

\* \* \* \* \*

UNITED STATES PATENT AND TRADEMARK OFFICE
CERTIFICATE OF CORRECTION

PATENT NO.        : 8,767,133 B2                         Page 1 of 1
APPLICATION NO.   : 13/202024
DATED             : July 1, 2014
INVENTOR(S)       : Hassan Sahouani et al.

It is certified that error appears in the above-identified patent and that said Letters Patent is hereby corrected as shown below:

On the Title Page, Column 2, Item (57) (Abstract)
Line 7, Delete "so" and insert -- so as --, therefor.

In the Specification

Column 2
Line 17, Delete "layer" and insert -- layer. --, therefor.

Column 3
Line 28, Delete "hydrophilic moities" and insert -- hydrophilic moieties --, therefor.

Column 19
Line 3, Delete "I" and insert -- IR --, therefor.

Signed and Sealed this
Fourteenth Day of April, 2015

Michelle K. Lee
*Director of the United States Patent and Trademark Office*